United States Patent
Princen et al.

(10) Patent No.: US 6,444,664 B1
(45) Date of Patent: Sep. 3, 2002

(54) METHOD FOR CONTROLLING THE PLASMA LEVEL OF LIPOPROTEINS TO TREAT ALZHEIMERIS DISEASE

(75) Inventors: Johannes Marinus Gerardus Princen, Oegstgeest; Take Kooistra, Leiden, both of (NL)

(73) Assignee: Nederlandse Organisatie voor Toegepast - Natuurweten Schappelijk Onderzoek (TNO), Delft (NL)

( * ) Notice: Subject to any disclaimer, the term of this patent is extended or adjusted under 35 U.S.C. 154(b) by 0 days.

(21) Appl. No.: 09/062,395

(22) Filed: Apr. 17, 1998

(30) Foreign Application Priority Data

Apr. 18, 1997 (EP) .............................. 97201139

(51) Int. Cl.⁷ ..................... A61K 31/55; A61K 31/54
(52) U.S. Cl. .................. 514/217.04; 514/212; 514/215; 514/220; 514/222; 514/824
(58) Field of Search ................ 514/212, 222, 514/220, 215, 217, 824, 211.08, 211.13, 212.05, 217.03, 217.08, 218, 217.04

(56) References Cited

U.S. PATENT DOCUMENTS 5,302,590 A    4/1994    Earley et al. ................ 514/220

FOREIGN PATENT DOCUMENTS

| EP | 402151 A1 | 12/1990 |
| EP | 459432 A1 | 12/1991 |
| WO | PCT/CH96/00001 | 7/1996 |

OTHER PUBLICATIONS

European Search Report, Nov., 1997.
Feliste et al., "Protective effect of BN 52021, a specific antagonist of platelet–activating factor (PAF–acether) against diet–induced cholesteryl ester deposition in rabbit aorta" Aetherosclerosis, vol. 78, 1989, Ireland, pp. 151–158.
M. Koltai et al., "Platelet Activating Factor (PAF): A review of its Effects, Antagonists and Possible Future Clinical Implications (Part I)", Drugs, vol. 42, No. 1, 1991, pp. 9–29.
M. Whittaker, "PAF Receptor Antagonists: Recent Advances", Current Opinion in Therapeutic Patents, vol. 2, No. 5, May 1, 1992, pp. 583–623.

Primary Examiner—Theodore J. Criares
(74) Attorney, Agent, or Firm—Handal & Morofsky

(57) ABSTRACT

A compound which is an antagonist of platelet activating factor (PAF-antagonist) or a structurally related compound thereof not having PAF-antagonistic activity can be used for decreasing the plasma level of lipoprotein(a) and/or increasing the plasma level of high-density lipoprotein. The compound may be an azepine derivative, especially a benzo- or thienotriazolo-diazepine derivative, a diphenyltetrahydrofuran or diphenyldioxolane derivative or a tetrahydrofuran phospholipid analogue.

21 Claims, No Drawings

METHOD FOR CONTROLLING THE PLASMA LEVEL OF LIPOPROTEINS TO TREAT ALZHEIMERIS DISEASE

FIELD OF THE INVENTION

The present invention relates to the use of active substances for preparing a medicament controlling the plasma level of the lipoproteins lipoprotein(a) (Lp(a)) and high-density lipoprotein (HDL) by decreasing the synthesis of apolipoprotein(a) (apo(a)) and by increasing the synthesis of apolipoprotein $A_1$ (apo $A_1$). In particular, the invention relates to the novel use of antagonists of platelet activating factor (PAF-antagonists) and of structurally related compounds, which do not necessarily possess PAF-antagonistic activity, for preparing such medicaments.

BACKGROUND

Apolipoprotein A-I (apo A-I) is the major protein constituent of plasma high density lipoprotein (HDL) (1). In mammals, the protein is mainly synthesized in the liver and the small intestine (1,2). Decreased plasma levels of HDL cholesterol are associated with an accelerated development of atherosclerotic lesions, which is, one of the main causes of coronary artery disease (3–5). The plasma level of apo A-I has been reported to be even more discriminatory in determining the risk of cardiovascular disease than the cholesterol concentration of HDL (6, 7).

Several drugs (e.g. fibrates and statins, summarized in refs. 5 and 12) are currently us use to lower plasma lipid levels, which secondarily increase plasma HDL levels. However, their HDL increasing effects are small in general and most of them, perhaps with the exception of gemfibrozil, appear to act indirectly, i.e. no direct effect on apo A-I synthesis is found (5,12). Recently, a series of urea-type compounds and thiazolo-[3,2-c]pyrimidine-5,7-diones have been claimed as HDL-elevators (see ref 95, 96 in 12).

A high plasma level of lipoprotein(a) (Lp(a)) is positively associated with the development of coronary heart disease and cerebrovascular disease in men and women, especially when plasma levels exceed 0,20–0,30 g/l and when LDL levels are concomitantly increased (13–15). In Lp(a) the apoprotein (a), which is synthesized in the liver, is covalently bound to an LDL particle. This binding is thought to take place extracellularly at the cell surface (12), in vivo turnover studies in humans indicated that Lp(a) levels are mainly influenced by Lp(a) and apo(a) production rates and not by Lp(a) clearance rates, emphasizing the importance of apo(a) synthesis for plasma Lp(a) levels (16, 17).

No satisfactory pharmacological treatment for raised Lp(a) levels exists currently. Of the established hypolipidemic drugs only nicotinic acid and perhaps some fibrates, as well as LDL apheresis treatment lower Lp(a) levels, but these therapies are inadequate in terms of efficacy, specificity and palatability (12, 14, 15).

Apo B-100 is the sole protein of LDL. Increased levels of LDL-cholesterol and apo B-100 in blood are strongly associated with the development of atherosclerosis and the incidence of coronary heart disease (8–11).

SUMMARY OF THE INVENTION

It was found that administration of certain compounds which have PAF (platelet activating factor) antagonistic activity and structurally related compounds, which may or may not have such activity, results in a reduced synthesis of apolipoprotein(a) (apo(a)) and/or, independently, in an enhanced synthesis of apolipoprotein $A_I$ (apo $A_I$).

DETAILED DESCRIPTION

In a first aspect the invention pertains to the use of compounds active as PAF-antagonists and structurally related compounds, which need not be active as PAF-antagonists, in the prevention and treatment of atherogenic conditions in mammals including man, by decreasing lipoprotein (a) (Lp(a)) levels in plasma. Such compounds may comprise azepine derivatives having the following formula 1:

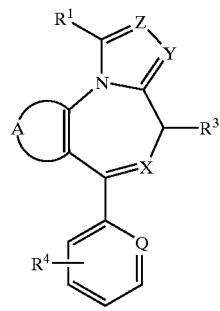

benzoazepine derivatives having the following formula 1a:

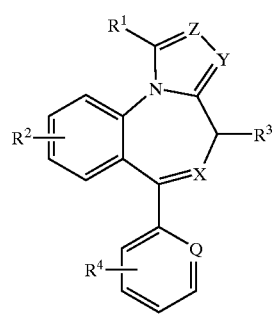

wherein A is a group —CH=C(R2)—CH=CH—, —S—C(R2)=CH—, —CH=C(R2)—S— or an optionally substituted benzo or thieno ring having the following formula 1b:

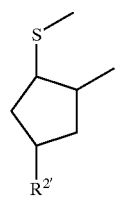

Q is a nitrogen atom (—N=), or an optionally substituted carbon atom (—CR$^4$=), R$^4$ being as defined below;

X is a nitrogen, sulphur or oxygen atom, the neighboring bond optionally being a double bond if X is nitrogen;

Y is a nitrogen atom (=N—) or an optionally substituted carbon atom (=CR—), having a substituent R wherein R is hydrogen, methyl, ethyl, methoxycarbonyl or ethoxycarbonyl;

Z is a nitrogen atom (—N=) or an optionally methyl-substituted carbon atom (—CR'=) having a substitutent R' wherein R$^1$ is hydrogen, methyl or hydroxymethyl;

at least one of Y and Z is a nitrogen atom;

R1 is hydrogen, halogen, $C_1$–$C_6$ alkyl, cycloalkylalkyl or cycloalkylalkenyl, trifluoromethyl, hydroxymethyl or aminomethyl, R2 is hydrogen, halogen, trifluoromethyl, nitro, $C_1$–$C_3$ alkyl or the group —CH2—CH2R$^2$, R$^{2'}$ being an optionally substituted phenyl, C1–C3 alkoxycarbonyl, or an aminomethyl or carbamoyl group, the nitrogen atom of the aminomethyl or carbamoyl group optionally being substituted by one or two $C_1$–$C_3$ alkyl groups or optionally being part of a pyrrolidino, piperidino, or morpholino ring;

R3 is hydrogen, hydroxyl, methyl or carboxyl; and

R4 is hydrogen, halogen, hydroxyl, methyl or methoxy;

and substituted tetrahydrofuran phospholipid analogues having the following formula 2:

2

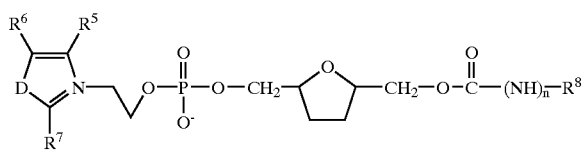

wherein D is —CR7=CR7— or —S—,

R5 and R6 are independently hydrogen, halogen, hydroxy, C1–C3 alkyl or C1–C3 alkoxy, or together are —(CH2)4—, —(CH)4— or —CH2OCH2—, each R7 is independently hydrogen, halogen, hydroxy, C1–C3 alkyl or C1–C3 alkoxy, R8 is C8–C20 alkyl, alkenyl, cycloalkyl-alkyl or arylalkyl, and n is 0 or 1, in particular the analogue denoted as PAF-antagonist SRI 63-441.

In a second aspect the invention pertains to such compounds in the prevention and treatment of atherogenic conditions by increasing HDL levels in plasma. It should be understand that, according to the invention, "structurally related" refers to compounds which have structural similarities, especially skeletal identity with the PAF-antagonists, but which need not be active as a PAF-antagonist.

Suitable PAF-antagonists are described, for example, by Hwang in *J. Lipid Mediators*, 2 (1990) 123–158 (ref. 18). Examples include various benzo- and thieno-diazepines, bis(trimethoxyphenyl)- or bis(dimethoxyphenyl)-dioxolanes and -tetrahydrofurans, especially trans-2,5bis(3, 4,5-trimethoxyphenyl)tetrahydrofuran (L-652,731) and cis- and trans-2,4-bis(3,4,5-trimethoxyphenyl)dioxolane, and various phospholipid analogues such as O-cis-5-(octadecylcarbamoyloxymethyl)-2-tetrahydrofurylmethyl O-(2-quinolinio-ethyl) hydrogen phosphate (SRI 63-441). These and other PAF-antagonists are also described by Saunders and Handley (ref. 19) and by Weber and Heuer (ref. 20).

The only effective pharmacological treatment known thus far for reducing Lp(a) levels, consists in administering nicotinic acid or its derivatives, either in combination with neomycine (3 g/day and 2 g/day respectively, see ref. 23) or alone (4 g/day, see ref. 24). Reductions of plasma levels of lp(a) were in the order of 45% and 38%, respectively.

The benzo- and thieno(di)azepines constitute an advantageous group of compounds for inhibiting apo(a) synthesis according to the invention. The benzo(di)azepines are also useful according to the invention for promoting apo A-I synthesis. Most of these compounds are known per se. Examples of specific (di)azepines and their synthesis are described in U.S. Pat. No. 5,302,590 and in WO 96/20941.

The known effects of the benzodiazepines virtually all result from the actions of the drugs on the central nervous system. The most prominent of these effects are sedation, hypnosis, decreased anxiety, muscle relaxation, anterograde amnesia, and anticonvulsant activity. Only two effects of the drugs appear to result from actions on peripheral tissues: coronary vasodilatation, seen after intravenous administration of therapeutic doses of certain benzodiazepines, and neuromuscular blockade, seen only with very high doses (cf. ref. 21).

It was reported in 1984 that psychotropic triazolobenzo-diazepines can inhibit the aggregation of platelets induced by platelet activating factor (22). Platelet-activating factor (PAF) is a potent inflammatory mediator with a wide variety of biological activities, such as induction of platelet and neutrophil aggregation, bronchoconstriction, hypotension and an increase in vascular permeability (19). Thus, PAF can induce a profile of biological effects which can mimic many of the major features of asthma. PAF-antagonists can be used in the management or prophylactic control of asthma or other inflammatory and allergic conditions (19,20). Many research groups were successful in separating CNS activity from PAF antagonism (20).

The benzo- and thieno- (di) azepines to be used according to the invention are defined in formulae 1, 1a and 1b above. It may be noted that the substituent represented by R$^2$ in the cyclopentane-2-yl-1-thyl group represented by symbol A may be substituted phenyl. Examples of substituents in this respect include alkyl, alkoxy, halo, hydroxyl, carbamoyl, carboxyl and alkoxycarbonyl and combinations thereof, such as a combination of N-{3-[2-(4-cycloalkyl-2-thiazolyl) ethenyl]phenyl} carbamoyl and carboxyl, ethoxycarbonyl or carbamoyl as described in U.S. Pat. No. 5,302,590.

The diphenyl-tetrahydrofuran and diphenyl-dioxolane derivatives, as well as the tetrahydrofuran phospholipids are another group of suitable compounds according to the invention, and are defined in formula 2 hereinabove.

The specificity of the reported effects is underlined by the absence of any effect on apo B-100 and albumin synthesis.

The pharmaceutical compositions to be prepared according to the invention may be formulated in the usual way, e.g. by associating the compounds with a pharmaceutically suitable solid or liquid carrier and optional adjuvants or other active components, stabilisers, colorants, flavourings etc. The composition may be suitable for oral administration (capsule, pill, tablet, gel, powder, sachet, syrup, solution, dispersion etc.) or may be an injectable solution or another administration form (e.g. via suppositories or via plasters). The effective dose is between 0.01 and 30 mg per kg body weight per day, preferably between 0.1 and 10 mg/kg.day. A dose can be administered in a single dosage or in several daily dosages.

Examples

Simian Hepatocyte Isolation and Culture

Simian hepatocytes were isolated from livers of both male and female monkeys. The monkeys were 1.5 to 3 years old and were obtained from the National Institute of Public Health and Environmental Protection (RIVM), Bilthoven, The Netherlands.

The monkeys were bred at the RIVM and served as donors for kidneys used in the production of poliomyelitis vaccine at this institute. The isolation procedure was performed as described previously (25). Viability, based on the ability of hepatocytes to exclude trypan blue dye (0.11%) was 66–96%. Total cell yields varied from 0.74 to $2.3 \times 10^9$ viable cells. The cells were seeded on culture dishes at a density of $1.5 \times 10^5$ viable cells per square cm and were maintained for the first 24 h in 1.5 mL per 10 square cm of Williams E medium supplemented with 10% heat inactivated (30 min at 56° C.) fetal calf serum (FCS) (Boehringer Mannheim), 2 mmol/L L-glutamine, 20 mU/mL insulin (135 nmol/L), 50 nmol/L dexamethasone, 100 U/mL penicillin, 100 μg/mL streptomycin and 100 μg/mL kanamycin at 37° C. in a 5% $CO_2$/95% air atmosphere. After 14–16 h the non-adherent cells were washed from the plates, using the same culture medium as described above. Twenty-four hours after seeding, the incubations with the compounds were started in 1 mL of the same culture medium, but with a lower insulin concentration, 10 nmol/L instead of 135 nmol/L. The medium was renewed every 24 h. At the end of each incubation period the medium was collected and 5 centrifuged for 30 seconds in an Eppendorf centrifuge at maximum speed to remove debris and detached cells. The supernatant was frozen in dry ice and stored at −20° C. until measurement of apolipoproteins. After the last incubation, the cells were washed three times with cold phosphate-buffered saline (PBS), pH 7.4, and cellular protein was determined. All incubations, control and with the compounds at various concentrations, were performed with medium containing 0.1% (v/v) DMSO. Materials used for the isolation and culturing of the simian hepatocytes were obtained front sources described previously (25).

Isolation and Culture of Human Hepatocytes

Human hepatocytes were isolated from pieces of livers, obtained from donors which could not be used for transplantation. Hepatocytes were isolated essentially as described previously in detail (26–28) and were cultured as described for simian hepatocytes, with the exception that incubations were started between 24 and 36 h after isolation of the hepatocytes.

Apo (a), apo A-I and apo B-100 ELISA

Total apo(a) concentrations were determined using the TintElize Lp(a) (Biopool AB, Umeå, Sweden). This ELISA uses polyclonal antibodies to human apo(a) both as catching and as detecting antibodies and detects in this manner free apo(a) as well as lp(a). The antibodies of this kit showed strong immunological cross-reactivity with lp(a) from cynomolgus monkeys with standard-curves parallel to human lp(a), indicating a high level of homology between human and cynomolgus lp(a), in accordance with Makino et at (29) and Azrolan et al (30).

Apo A-1 and apo B-100 concentrations in the medium were measured using a sandwich enzyme-linked immunosorbent assay (ELISA) with polyclonal antibodies to human apo A-I or human apo B-100, respectively, both as catching and detecting antibodies as described previously (31,32). The standard curves for apo A-I and apo B-100 in human and cynomolgus monkey sera and in medium of cultured cynomolgus and human hepatocytes were parallel, indicating that similar epitopes on apo A-I and apo B-100 of the two species are recognized.

Data shown in table 1 are obtained from measurements in media of hepatocytes cultured for 72 h with or without the compounds, i.e. culture period from 48 h to 72 h.

RNA Hybridization

Total RNA was isolated from cynomolgus hepatocytes, cultured for 48 h in the presence or absence of the compounds, by the method of Chomczynski & Sacchi (33). After washing the RNA pellets with 70% (v/v) ethanol, RNA samples were dissolved in water. The RNA concentration in each sample was determined spectrophotometrically, assuming that one $A_{260}$ unit corresponds with 40 μg RNA/mL. Equal amounts of total RNA (10 μg) from different incubations were fractionated by, elcctrophoresis in a 0.8% (w/v) agarose gel containing 0.27 M formaldehyde, and transferred to Hybond-N+ (Amershamn) in accordance with the manufacturer's instructions and UV cross-linked. Probes, labelling conditions and hybridization were performed as described previously in detail (25).

Apo(a) mRNAs were detected using a kringle IV synthetic double-stranded probe of 75 nucleotides with the sense sequence: GGGAATTCGA ACCTGCCAAG CTTG-GTCATC TATGACACCA CACTCGCATA GTCGGAC-CCC AGAATAAAGCTTGGG, based on the sequence published by McLean et al (34). This probe was labelled by the random primer method according to Megaprime™ DNA labelling systems (Amersham). After hybridization, the blots were washed twice with 2×SSC/1% SDS (1×SSC=0.15 mol/L NaCl/0.015 mol/L sodium citrate, pH 7.0) and twice with 1×SSC/1% SDS for 30 min at 65° C. The blots were exposed to a Fuji imaging plate type BAS-MP for 1 to 24 h. The relative amounts of mRNA were quantified using a phospho-imager (Fuji Fujix BAS 1000) and the computer programs BAS-reader version 2.8 and TINA version 2.08 c.

Data shown in table 2 are obtained from measurements using RNA isolated from hepatocytes cultured for 48 h with or without the compounds.

TABLE 1

Effects of the compounds on synthesis of apo A-I, apo(a) and apo B-100 by cynomolgus monkey and human hepatocytes

| Compound | Conc. μM | Apo A-I | Apo(a) % of control[1] | Apo B-100 |
|---|---|---|---|---|
| Synthesis in cynomolgus (simian) hepatocytes | | | | |
| Azepine 1[2] | 3 | 152 ± 30 (2) | 85 ± 5 (2) | 117 ± 10 (2) |
| | 10 | 185 ± 20 (6) | 76 ± 19 (6) | 113 ± 20 (6) |
| | 30 | 225 ± 45 (6) | 48 ± 28 (6) | 106 ± 27 (6) |
| | 100 | 367 ± 131 (6) | 34 ± 32 (6) | 95 ± 23 (6) |
| Azepine 2[2] | 30 | 178 (1) | no change | not tested |
| Azepine 3[2] | 100 | 359 ± 74 (3) | 42 ± 20 (3) | 102 ± 32 (2) |
| Azepine 4[2] | 100 | 390 ± 40 (2) | 62 ± 22 (2) | 95 ± 23 (2) |
| Transdioxolane[3] | 30 | 116 ± 7 (3) | 103 ± 9 (3) | 117 ± 23 (3) |
| | 100 | 157 ± 2 (3) | 60 ± 12 (3) | 105 ± 7 (3) |
| Cisdioxolane[4] | 100 | 229 ± 79 (2) | 83 ± 2 (3) | 99 ± 21 (3) |
| L-652,731[5] | 100 | 134 ± 1 (2) | 66 ± 8 (2) | 76 ± 35 (2) |
| SRI 63-441[6] | 100 | 166 ± 6 (2) | 24 ± 1 (2) | 142 ± 32 (2) |
| BN 52051[7] | 100 | 144 ± 34 (2) | 101 ± 1 (2) | 113 ± 34 (2) |
| Synthesis in human hepatocytes | | | | |
| Azepine 1[2] | 3 | 164 ± 61 (2) | 75 (1) | 83 ± 16 (2) |
| | 10 | 283 ± 109 (2) | 48 (1) | 112 ± 3 (2) |
| | 30 | 622 ± 228 (2) | 24 (1) | 109 ± 8 (2) |
| | 100 | 721 ± 212 (2) | 14 (1) | 114 ± 8 (2) |

[1]Values are means ± S.D. or range of duplicate incubations of the number of independent culture experiments indicated in parentheses.
[2]Azepine 1 has formula 1, A = CH=CH—S, X = Y = Z = N, $R^1$ = $CH_3$, $R^3$ = $R^4$ = H
Azepine 2 has formula 1, A = CH=CH—S, X = Y = Z = N, $R^1$ = $R^3$ = $R^4$ = H
Azepine 3 has formula 1, A = CH=CH—CCl=CH, X = Y = Z = N, $R^1$ = $CH_3$, $R^3$ = $CH_3$, $R^4$ = H
Azepine 4 has formula 1, A = CH=CH—CH=CH, X = Y = Z = N, $R^1$ = Br, $R^3$ = $R^4$ = H
[3]Trans-2,4-bis(3,4,5-trimethoxyphenyl)dioxolane, commercially available
[4]Cis-2,4-bis(3,4,5-trimethoxyphenyl)dioxolane, commercially available
[5]Trans-2,5-bis(3,4,5-trimethoxyphenyl)tetrahydrofuran

TABLE 1-continued

Effects of the compounds on synthesis of apo A-I, apo(a) and apo B-100 by cynomolgus monkey and human hepatocytes

| Compound | Conc. µM | Apo A-I | Apo(a) % of control[1] | Apo B-100 |
|---|---|---|---|---|

[6]The phospholipid analogue with formula 2, wherein Z is vinylene. $R^5$ and $R^6$ together form benzo[b], $R^7$ is hydrogen, $R^8$ is octadecyl and n is 1,
[7]Ginkgolide B, commercially available

TABLE 2

Effect of azepine 1 on mRNA levels of apo A-I and apo(a) in cynomolgus monkey and human hepatocytes

| Compound | Conc. µM | % of control[1] Apo A-I | Apo(a) |
|---|---|---|---|
| mRNA levels relative to rRNA in cynomolgus (simian) hepatocytes | | | |
| azepine 1 | 100 | 229 ± 8 (3) | 56 ± 12 (3) |
| mRNA levels relative to GAPDH in cynomolgus (simian) hepatocytes | | | |
| azepine 1 | 100 | 147 ± 28 (3) | 39 ± 4 (3) |
| mRNA levels relative to actin in cynomolgus (simian) hepatocytes | | | |
| azepine 1 | 100 | 328 ± 7 (3) | 86 ± 7 (3) |
| mRNA levels relative to rRNA in human hepatocytes | | | |
| azepine 1 | 100 | 308 (1) | 67 (1) |
| mRNA levels relative to GAPDH in human hepatocytes | | | |
| azepine 1 | 100 | 111 (1) | 24 (1) |
| mRNA levels relative to actin in human hepatocytes | | | |
| azepine 1 | 100 | 203 (1) | 44 (1) |

[1]Values are means ± S.D. of the number of independent culture experiments indicated in the parentheses.
The increased apo A-I mRNA levels indicate that the increased apo A-I synthesis is regulated at the (post)-transcription level.
The decreased apo(a) mRNA levels indicate that the decreased apo(a) synthesis is regulated at the (post)-transcription level.

References

1. Eisenberg S: J Lipid Res 1984; 25: 1017–1058.
2. Brewer H B Jr, Fairwell T, LaRue A, Ronan R, Houser A, Bronzert T J: Biochem Biophys Res Commun 1978; 80: 623–630.
3. Gordon T, Castelli W P, Hjortland M C, Kannel W B, Dawbei T R: Am J Med 1977; 62: 707–714.
4. Breslow J L: Familial disorders of high density lipoprotein metabolism, in The Metabolic Basis of Inherited Disease (Scriver CR, Beaudet AL, Sly WS, Valle D, Eds). McGraw-Hill, New York, 1989: pp 1251–1266.
5. Gordon D J, Rifkind B M: N Engl J Med 1989; 321: 1311–1316.
6. Glueck C J, Gartside P, Fallat R W, Sielski J, Steiner P M: J Lab Clin Med 1976; 88: 941–957.
7. Brunzell J D, Sniderman A D, Albers J J, Kwiterovich P O Jr: Arteriosclerosis 1984; 4: 79–83,
8. Lipid Research Clinics Programme: the Lipid Research Clinics Coronary Prevention Trial Results: II. The relationship of reduction in incidence of coronary heart disease to cholesterol lowering. JAMA 1984; 251: 365–374.
9. Kesaniemi Y A, Grundy S M: Arteriosclerosis 1983; 3. 40–46.
10. Teng B, Sniderman A D, Soutar A K, Thompson G R: J Clin Invest 1986; 77: 663–672.
11. Castelli W P, Garrison R J, Wilson P W F, Abbott R D, Kalousdian S, Kannel W B: JAMA 1986; 256: 2835–2838.
12. Krause B R, Sliskovic D R, Bocan T M A: Emerging therapies in atherosclerosis. Exp Opin Invest Drugs 1995; 4: 353–387.
13. Dahlén G H: Atherosclerosis 1994; 108: 111–126.
14. Berglund L: Curr Opin Lipidol 1995: 6: 48–56.
15. Maher V M G, Brown B G: Curr Opin Lipidol 1995; 6: 229–235.
16. Krempler F, Kostner G M, Bolzano K, Sandhofer F: J Clin Invest 1980; 65: 1483–1490.
17. Rader D J, Cain W, Ikewaki K, Talley G, Zech L A, Usher D, Brewer H B Jr: J Clin Invest 1994; 93: 2758–2763.
18. Hwang S B, J. Lipid Mediators, 1990: 2: 123–158.
19. Saunders R N, Handley D A. Ann Rev Pharmacol Toxicol 1987; 27: 237–255.
20. Weber K H, Heuer H O. Med Res Rev 1989; 9: 181–218.
21. Goodman & Gilman's The pharmacological basis of therapeutics. Eds. Hardman J G, Limbird L E, Molinoff P B, Ruddon R W, Goodman Gilman A. 9th edition 1996. McGraw-Hill, New York.
22. Kornecki E, Ehrlich Y, Lenox R H. Science 1984; 226: 1454–1456.
23. Gurakar A, Hoeg J M, Kostner G, Papadopoulos N M, Brewer H B. Atherosclerosis 1985; 57; 293–301
24. Carlson L A, Hamsten A, Asplund A. J Intern Med 1989; 226: 271–276
25. Kaptein A, de Wit E C M, Princen H M G. Arterioscler Thromb. 1993;13:1505–1514.
26. Princen H M G, Huijsmans C M G, Kuipers F, Vonk R J, Kempen H J M. J Clin Invest 1986; 78: 1064–1071
27. Havekes L M, Verboom H, de Wit E, Yap S H, Princen H M G. Hepatology 1986; 6: 1356–1360
28. Kooistra T, Bosma P J, Tons H A M, van den Berg A P, Meijer P, Princen H M G. Thromb Haemostas 1989; 62: 723–728
29. Makino K, Abe A, Maeda S, Noma A, Kawada M, Takenaka O. Atherosclerosis. 1989; 78: 81–85.
30. Azrolan N, Gavish D, Breslow J L. J Biol Chem. 1991; 266: 13866–13872.
31. Kaptein A, Roodenburg L, Princen H M G. Biochem J. 1991; 278: 557–564.
32. Kaptein A, de Wit E C M, Princen H M G. Arterioscler Thromb. 1994; 14: 780–789
33. ChomczyInski P, Sacchi N. Anal Biochem 1987; 162: 156–159.
34. McLean J W, Tomlinson J E, Kuang W J, Eaton D L, Chen E Y, Fless G M, Scanu A M, Lawn R M. Nature 1987; 300: 132–137.

What is claimed is:

1. A method for treating or preventing atherosclerotic conditions comprising decreasing the synthesis of apolipoprotein(a) or decreasing the plasma level of lipoprotein(a) or increasing the synthesis of apolipoprotein A1 or increasing the plasma level of high-density lipoprotein by administering an effective amount of a compound selected from the group consisting of azepine derivatives having the following formula 1:

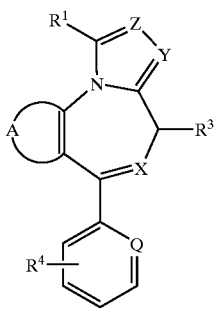

and of benzoazepine derivatives having the following formula 1a:

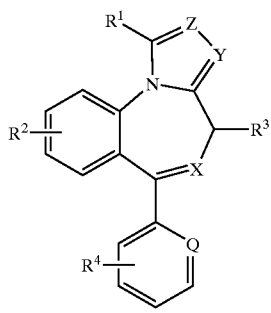

wherein, in formula 1, A is a group —CH=C(R2)—CH=CH—, —S—C(R2)=CH—, —CH=C(R2)—S— or an optionally substituted benzo or thieno ring having the following formula 1b:

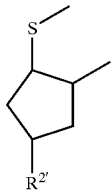

Q is a nitrogen atom (—N=), or an optionally substituted carbon atom (—CR$^4$=), R$^4$ being as defined below;

X is a nitrogen, sulphur or oxygen atom, the neighboring bond optionally being a double bond if X is nitrogen;

Y is a nitrogen atom (=N—) or an optionally substituted carbon atom (=CR—), having a substituent R wherein R is hydrogen, methyl, ethyl, methoxycarbonyl or ethoxycarbonyl;

Z is a nitrogen atom (—N=) or an optionally methyl-substituted carbon atom (—CR$^1$=) having a substituent R' wherein R$^1$ is hydrogen, methyl or hydroxymethyl;

at least one of Y and Z is a nitrogen atom;

R1 is hydrogen, halogen, $C_1$–$C_6$ alkyl, cycloalkylalkyl or cycloalkylalkenyl, trifluoromethyl, hydroxymethyl or aminomethyl, R2 is hydrogen, halogen, trifluoromethyl, nitro, $C_1$–$C_3$ alkyl or the group —CH2—CH2R$^2$, R$^2{'}$ being an optionally substituted phenyl, C1–C3 alkoxycarbonyl, or an aminomethyl or carbamoyl group, the nitrogen atom of the aminomethyl or carbamoyl group optionally being substituted by one or two $C_1$–$C_3$ alkyl groups or optionally being part of a pyrrolidino, piperidino, or morpholino ring;

R3 is hydrogen, hydroxyl, methyl or carboxyl; and

R4 is hydrogen, halogen, hydroxyl, methyl or methoxy.

2. A method according to claim 1, wherein R1 is hydrogen, halogen or methyl and/or R3 is hydrogen or methyl.

3. A method according to claim 1, wherein R2 is hydrogen or halogen.

4. A method according to claim 1, wherein Q is —CR4= and R4 is hydrogen, 2-chloro or 3-hydroxy.

5. A method according to claim 1, wherein X is nitrogen, the neighboring bond being a double bond, and/or Y and Z are both nitrogen.

6. A method according to claim 1, comprising a combination of at least two of decreasing the synthesis of apolipoprotein(a), decreasing the plasma levels of lipoprotein(a), increasing the synthesis of apolipoprotein A1 and increasing the plasma level of high-density lipoprotein.

7. A method according to claim 1, wherein said effective amount is between 0.01 and 30 mg per kg body weight per day.

8. A method according to claim 1, wherein said effective amount is between 0.1 and 10 mg per kg body weight per day.

9. A method according to claim 1, wherein the compound is an azepine having formula 1 and wherein A is —CH=CH—S—; X, Y and Z are all =N—; R$^1$ is —CH$_3$ and R$^3$ and R$^4$ are both hydrogen.

10. A method according to claim 1, wherein the compound is an azepine having formula 1 and wherein A is —CH=CH—S—; X, Y and Z are all =N—; and R$^1$, R$^3$ and R$^4$ are all hydrogen.

11. A method according to claim 1, wherein the compound is an azepine having formula 1 and wherein A is —CH=CCL=CH—; X, Y and Z are all =N—; R$^1$ and R$^3$ are —CH$_3$; and R$^4$ is hydrogen.

12. A method according to claim 1, wherein the compound is an azepine having formula 1 and wherein A is —CH=CH—CH=CH—; X, Y and Z are all =N—; R$^1$ is Br; and R$^3$ and R$^4$ are both hydrogen.

13. A method according to claim 1, wherein the compound is administered to a primate.

14. A method according to claim 1, wherein the synthesis of apolipoprotein(a) is decreased.

15. A method according to claim 1, the synthesis of apolipoprotein A1 or the plasma level of high-density lipoprotein is increased.

16. A method according to claim 1, wherein the synthesis of apolipoprotein(a) is decreased and the synthesis of apolipoprotein A1 and the plasma level of high-density lipoprotein are increased.

17. A method according to claim 1 comprising decreasing the synthesis of apolipoprotein(a) and/or decreasing the plasma levels of lipoprotein(a) and/or increasing the synthesis of apolipoprotein A1 and/or increasing the plasma level of high-density lipoprotein.

18. A method of treating or preventing atherosclerotic conditions, being non-thrombotic conditions, the method being effected via a mode of action selected from the group consisting of decreasing the synthesis of lipoprotein(a), decreasing the plasma level of lipoprotein(a), increasing the synthesis of apolipoprotein A1, increasing the plasma level of high-density lipoprotein and combinations of the foregoing modes, the method comprising administering to a patient in need thereof, an effective amount of a benzoazepine derivative having the following formula 1a:

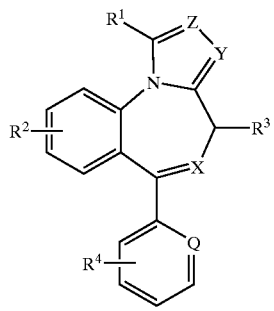

wherein
- Q is a nitrogen atom (—N═) or an optionally substituted carbon atom (—CR⁴═);
- X is a nitrogen, sulphur or oxygen atom, the neighboring bond optionally being a double bond if X is nitrogen;
- Y is a nitrogen atom (═N—) or an optionally substituted carbon atom (═CR—), wherein R is hydrogen, methyl, ethyl, methoxycarbonyl or ethoxycarbonyl;
- Z is a nitrogen atom (—N═) or an optionally methyl-substituted carbon atom (—CR¹═) wherein R' is hydrogen, methyl or hydroxymethyl; at least one of Y and Z being a nitrogen atom;
- $R^1$ is hydrogen, halogen, $C_1$–$C_6$ alkyl, cycloalkylalkyl or cycloalkylalkenyl, trifluoromethyl, hydroxymethyl or aminomethyl;
- $R^2$ is hydrogen, halogen, trifluoromethyl, nitro, $C_1$–$C_3$ alkyl or a group —CH$_2$—CH$_2$R$^{2'}$;
- $R^{2'}$ is optionally a substituted phenyl, $C_1$–$C_3$ alkoxycarbonyl, or an aminomethyl or carbamoyl group, the nitrogen atom of the aminomethyl or carbamoyl group optionally being substituted by one or two $C_1$–$C_3$ alkyl groups or optionally being part of a pyrrolidino, piperidino, or morpholino ring;
- $R^3$ is hydrogen, hydroxyl, methyl or carboxyl; and
- $R^4$ is hydrogen, halogen, hydroxyl, methyl or methoxy.

19. A method according to claim 18, wherein $R^1$ is hydrogen, halogen or methyl $R^2$ is hydrogen or halogen and/or $R^3$ is hydrogen or methyl.

20. A method according to claim 18, wherein Q is —CR⁴═, $R^4$ is hydrogen, 2-chloro or 3-hydroxy and X, Y and Z are nitrogen, the neighboring bond of X being a double bond.

21. A method according to claim 18, wherein said effective amount is between 0.01 and 30 mg per kg body weight and the method comprises administering the benzoazepine derivative to a primate.

* * * * *

UNITED STATES PATENT AND TRADEMARK OFFICE
CERTIFICATE OF CORRECTION

| | | |
|---|---|---|
| PATENT NO. | : 6,444,664 B1 | |
| DATED | : September 3, 2002 | |
| INVENTOR(S) | : Johannes Marinus Gerardus Princen et al. | |

It is certified that error appears in the above-identified patent and that said Letters Patent is hereby corrected as shown below:

<u>Title page,</u>
Item [54], Title, should read as following;
-- METHOD FOR CONTROLLING PLASMA LEVEL OF LIPOPROTEINS --

Signed and Sealed this

Eighth Day of July, 2003

JAMES E. ROGAN
*Director of the United States Patent and Trademark Office*